(12) United States Patent
Benson (10) Patent No.: US 10,207,126 B2
(45) Date of Patent: Feb. 19, 2019

(54) LUMEN VISUALIZATION AND IDENTIFICATION SYSTEM FOR MULTI-LUMEN BALLOON CATHETER

(75) Inventor: Maria Benson, West Boylston, MA (US)

(73) Assignee: CYTYC CORPORATION, Marlborough, MA (US)

( * ) Notice: Subject to any disclaimer, the term of this patent is extended or adjusted under 35 U.S.C. 154(b) by 886 days.

(21) Appl. No.: 12/463,463

(22) Filed: May 11, 2009

(65) Prior Publication Data

US 2010/0286465 A1 Nov. 11, 2010

(51) Int. Cl.
| | |
|---|---|
| A61N 5/00 | (2006.01) |
| A61N 5/10 | (2006.01) |
| A61M 25/00 | (2006.01) |
| A61M 25/01 | (2006.01) |
| A61M 25/10 | (2013.01) |
| A61B 90/00 | (2016.01) |

(52) U.S. Cl.
CPC ....... *A61N 5/1015* (2013.01); *A61M 25/0029* (2013.01); *A61B 90/39* (2016.02); *A61M 25/0108* (2013.01); *A61M 25/10* (2013.01); *A61M 2025/004* (2013.01); *A61N 2005/1018* (2013.01)

(58) Field of Classification Search
CPC ...................... A61M 25/0029; A61M 25/0108
USPC ................ 600/1, 3, 585, 4, 6; 128/897, 898; 604/103.03, 117
See application file for complete search history.

(56) References Cited

U.S. PATENT DOCUMENTS

| | | | |
|---|---|---|---|
| 3,324,847 A | 6/1967 | Zoumboulis | |
| 3,502,878 A | 3/1970 | Stewart | |
| 3,863,073 A | 1/1975 | Wagner | |
| 3,872,856 A | 3/1975 | Clayton | |
| 3,971,950 A | 7/1976 | Evans et al. | |

(Continued)

FOREIGN PATENT DOCUMENTS

| | | |
|---|---|---|
| DE | 25 39 553 | 3/1977 |
| EP | 0 340 881 | 10/1992 |

(Continued)

OTHER PUBLICATIONS

Ashpole, et al., "A New Technique of Brachytherapy for Malignant Gliomas with Caesium-137: A New Method Utilizing a Remote Afterloading System," Clinical Oncology, p. 333-337.

(Continued)

*Primary Examiner* — John Lacyk (57) ABSTRACT

Systems and methods that facilitate visualization and identification of lumens of a multi-lumen brachytherapy device are disclosed. In one embodiment, visualization and identification can be attained by modifying a feature of at least one of the lumens relative to the other lumens. The feature may include a marking on the lumen, a diameter of the lumen or a composition of the lumen. In an additional embodiment, for brachytherapy devices in which multiple lumens are coupled to a distal end point such as a rigid connection member, visualization and identification of the lumens can be attained by modifying a feature of the rigid connection member. It will be readily appreciated that visualization and identification can be further enhanced through a combination of two or more of the techniques described herein.

18 Claims, 4 Drawing Sheets

(56) References Cited

U.S. PATENT DOCUMENTS

| | | |
|---|---|---|
| 3,975,350 A | 8/1976 | Hudgin et al. |
| 4,119,094 A | 10/1978 | Micklus et al. |
| 4,160,906 A | 7/1979 | Daniels et al. |
| 4,310,766 A | 1/1982 | Finkenzeller et al. |
| 4,350,169 A | 9/1982 | Dutcher et al. |
| 4,417,576 A | 11/1983 | Baran |
| 4,454,106 A | 6/1984 | Gansow et al. |
| 4,496,557 A | 1/1985 | Malen et al. |
| 4,559,641 A | 12/1985 | Caugant et al. |
| 4,571,241 A | 2/1986 | Christopher |
| 4,690,677 A | 9/1987 | Erb |
| 4,706,269 A | 11/1987 | Reina et al. |
| 4,706,652 A | 11/1987 | Horowitz |
| 4,744,099 A | 5/1988 | Huettenrauch et al. |
| 4,754,745 A | 7/1988 | Horowitz |
| 4,763,642 A | 8/1988 | Horowitz |
| 4,773,086 A | 9/1988 | Fujita et al. |
| 4,773,087 A | 9/1988 | Plewes |
| 4,819,258 A | 4/1989 | Kleinman et al. |
| 4,821,725 A | 4/1989 | Azam et al. |
| 4,821,727 A | 4/1989 | Levene et al. |
| 4,867,741 A | 9/1989 | Portnoy |
| 4,929,470 A | 5/1990 | Rittenhouse et al. |
| 4,969,174 A | 11/1990 | Scheid et al. |
| 4,989,227 A | 1/1991 | Tirelli et al. |
| 4,998,917 A | 3/1991 | Geiser et al. |
| 4,998,930 A | 3/1991 | Lundahl |
| 5,015,247 A | 5/1991 | Michaelson |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,059,166 A | 10/1991 | Fischell et al. |
| 5,078,142 A | 1/1992 | Siczek et al. |
| 5,084,001 A | 1/1992 | Van 't Hooft et al. |
| 5,084,015 A | 1/1992 | Moriuchi |
| 5,084,022 A * | 1/1992 | Claude .................... 604/164.13 |
| 5,106,360 A | 4/1992 | Ishiwara et al. |
| 5,112,303 A | 5/1992 | Pudenz et al. |
| 5,152,747 A | 10/1992 | Olivier |
| 5,163,075 A | 11/1992 | Lubinsky et al. |
| 5,164,976 A | 11/1992 | Scheid et al. |
| 5,167,622 A | 12/1992 | Muto |
| 5,199,056 A | 3/1993 | Darrah |
| 5,199,939 A | 4/1993 | Dake et al. |
| 5,227,969 A | 7/1993 | Waggener et al. |
| 5,236,410 A | 8/1993 | Granov et al. |
| 5,240,011 A | 8/1993 | Assa |
| 5,259,847 A | 11/1993 | Trambert |
| 5,289,520 A | 2/1994 | Pellegrino et al. |
| 5,302,168 A | 4/1994 | Hess |
| 5,312,356 A | 5/1994 | Engelson et al. |
| 5,314,518 A | 5/1994 | Ito et al. |
| 5,336,178 A | 8/1994 | Kaplan et al. |
| 5,342,305 A | 8/1994 | Shonk |
| 5,359,637 A | 10/1994 | Webber |
| 5,365,562 A | 11/1994 | Toker |
| 5,381,504 A | 1/1995 | Novack et al. |
| 5,411,466 A | 5/1995 | Hess |
| 5,415,169 A | 5/1995 | Siczek et al. |
| 5,417,687 A | 5/1995 | Nardella et al. |
| 5,422,926 A | 6/1995 | Smith et al. |
| 5,426,685 A | 6/1995 | Pellegrino et al. |
| 5,428,658 A | 6/1995 | Oettingger et al. |
| 5,429,582 A | 7/1995 | Williams |
| 5,452,367 A | 9/1995 | Bick et al. |
| 5,465,733 A | 11/1995 | Hinohara |
| 5,484,384 A | 1/1996 | Fearnot |
| 5,503,613 A | 4/1996 | Weinberger |
| 5,506,877 A | 4/1996 | Niklason et al. |
| 5,520,646 A | 5/1996 | D'Andrea |
| 5,526,394 A | 6/1996 | Siczek et al. |
| 5,535,817 A | 7/1996 | Dunne |
| 5,539,797 A | 7/1996 | Heidsieck et al. |
| 5,553,111 A | 9/1996 | Moore et al. |
| 5,562,594 A | 10/1996 | Weeks |
| 5,566,221 A | 10/1996 | Smith |
| 5,592,562 A | 1/1997 | Rooks |
| 5,594,769 A | 1/1997 | Pellegrino et al. |
| 5,596,200 A | 1/1997 | Sharma et al. |
| 5,598,454 A | 1/1997 | Franetzki et al. |
| 5,603,991 A | 2/1997 | Kupiecki et al. |
| 5,609,152 A | 3/1997 | Pellegrino et al. |
| 5,611,767 A | 3/1997 | Williams |
| 5,616,114 A | 4/1997 | Thornton et al. |
| 5,621,780 A | 4/1997 | Smith et al. |
| 5,624,395 A | 4/1997 | Mikhail et al. |
| 5,627,869 A | 5/1997 | Andrew et al. |
| 5,653,683 A | 8/1997 | D'Andrea |
| 5,657,362 A | 8/1997 | Giger et al. |
| 5,662,580 A | 9/1997 | Bradshaw et al. |
| 5,668,889 A | 9/1997 | Hara |
| 5,704,926 A | 1/1998 | Sutton |
| 5,706,327 A | 1/1998 | Adamkowski et al. |
| 5,719,952 A | 2/1998 | Rooks |
| 5,720,717 A | 2/1998 | D'Andrea |
| 5,724,400 A | 3/1998 | Swerdloff et al. |
| 5,735,264 A | 4/1998 | Siczek et al. |
| 5,741,253 A | 4/1998 | Michelson |
| 5,759,173 A | 6/1998 | Preissman et al. |
| 5,769,086 A | 6/1998 | Ritchart et al. |
| 5,782,742 A | 7/1998 | Crocker et al. |
| 5,800,333 A | 9/1998 | Liprie |
| 5,803,895 A | 9/1998 | Kronholz et al. |
| 5,803,912 A | 9/1998 | Siczek et al. |
| 5,818,898 A | 10/1998 | Tsukamoto et al. |
| 5,820,594 A | 10/1998 | Fontirroche et al. |
| 5,820,717 A | 10/1998 | Siegenthaler |
| 5,828,722 A | 10/1998 | Ploetz et al. |
| 5,851,182 A | 12/1998 | Sahadevan |
| 5,863,284 A | 1/1999 | Klein |
| 5,863,285 A | 1/1999 | Coletti |
| 5,872,828 A | 2/1999 | Niklason et al. |
| 5,878,104 A | 3/1999 | Ploetz |
| 5,896,437 A | 4/1999 | Ploetz |
| 5,899,882 A | 5/1999 | Waksman et al. |
| 5,908,406 A | 6/1999 | Ostapchenko et al. |
| 5,913,813 A | 6/1999 | Williams et al. |
| 5,916,143 A | 6/1999 | Apple et al. |
| 5,919,473 A | 7/1999 | Elkhoury |
| 5,924,973 A | 7/1999 | Weinberger |
| 5,931,774 A | 8/1999 | Williams et al. |
| 5,935,098 A | 8/1999 | Blaisdell et al. |
| 5,986,662 A | 11/1999 | Argiro et al. |
| 5,993,972 A | 11/1999 | Reich et al. |
| 6,005,907 A | 12/1999 | Ploetz |
| 6,013,038 A | 1/2000 | Pflueger |
| 6,022,308 A | 2/2000 | Williams |
| 6,022,325 A | 2/2000 | Siczek et al. |
| 6,033,357 A | 3/2000 | Ciezki et al. |
| 6,036,631 A | 3/2000 | McGrath et al. |
| 6,050,930 A | 4/2000 | Teirstein |
| 6,056,702 A | 5/2000 | Lorenzo |
| 6,075,879 A | 6/2000 | Roehrig et al. |
| 6,083,148 A | 7/2000 | Williams |
| 6,086,970 A | 7/2000 | Ren |
| 6,091,841 A | 7/2000 | Rogers et al. |
| 6,093,142 A | 7/2000 | Ciamacco, Jr. |
| 6,095,966 A | 8/2000 | Chomenky et al. |
| 6,137,527 A | 10/2000 | Abdel-Malek et al. |
| 6,141,398 A | 10/2000 | He et al. |
| 6,143,013 A | 11/2000 | Samson et al. |
| 6,149,301 A | 11/2000 | Kautzer et al. |
| 6,175,117 B1 | 1/2001 | Komardin et al. |
| 6,196,715 B1 | 3/2001 | Nambu et al. |
| 6,200,257 B1 | 3/2001 | Winkler |
| 6,216,540 B1 | 4/2001 | Nelson et al. |
| 6,217,565 B1 | 4/2001 | Cohen |
| 6,219,059 B1 | 4/2001 | Argiro |
| 6,233,473 B1 | 5/2001 | Shepherd et al. |
| 6,234,952 B1 | 5/2001 | Liprie |
| 6,243,441 B1 | 6/2001 | Zur |
| 6,248,122 B1 | 6/2001 | Klumb et al. |
| 6,251,059 B1 | 6/2001 | Apple et al. |

(56) References Cited

U.S. PATENT DOCUMENTS

| | | |
|---|---|---|
| 6,256,370 B1 | 7/2001 | Yavuz |
| 6,256,529 B1 | 7/2001 | Holupka et al. |
| 6,267,775 B1 | 7/2001 | Clerc et al. |
| 6,272,207 B1 | 8/2001 | Tang |
| 6,282,142 B1 | 8/2001 | Miyawaki |
| 6,289,235 B1 | 9/2001 | Webber et al. |
| 6,292,530 B1 | 9/2001 | Yavus et al. |
| 6,306,074 B1 | 10/2001 | Waksman et al. |
| 6,319,188 B1 | 11/2001 | Lovoi |
| 6,327,336 B1 | 12/2001 | Gingold et al. |
| 6,341,156 B1 | 1/2002 | Baetz et al. |
| 6,375,352 B1 | 4/2002 | Hewes et al. |
| 6,378,137 B1 | 4/2002 | Hassan et al. |
| 6,390,967 B1 | 5/2002 | Forman et al. |
| 6,390,968 B1 | 5/2002 | Harmon |
| 6,390,992 B1 | 5/2002 | Morris et al. |
| 6,398,708 B1 | 6/2002 | Hastings et al. |
| 6,411,836 B1 | 6/2002 | Patel et al. |
| 6,413,203 B1 | 7/2002 | Sahatjian |
| 6,413,204 B1 | 7/2002 | Winkler et al. |
| 6,415,015 B2 | 7/2002 | Nicolas et al. |
| 6,416,457 B1 | 7/2002 | Urick et al. |
| 6,416,492 B1 | 7/2002 | Nielson |
| 6,442,288 B1 | 8/2002 | Haerer et al. |
| 6,443,912 B1 | 9/2002 | Mazzola et al. |
| 6,458,069 B1 | 10/2002 | Tam et al. |
| 6,458,070 B1 | 10/2002 | Waksman et al. |
| 6,459,925 B1 | 10/2002 | Nields et al. |
| 6,482,142 B1 | 11/2002 | Winkler et al. |
| 6,501,819 B2 | 12/2002 | Unger et al. |
| 6,512,942 B1 | 1/2003 | Burdette et al. |
| 6,527,693 B2 | 3/2003 | Munro, III et al. |
| 6,540,655 B1 | 4/2003 | Chin et al. |
| 6,556,655 B1 | 4/2003 | Chichereau et al. |
| 6,558,390 B2 | 5/2003 | Cragg |
| 6,579,221 B1 * | 6/2003 | Peterson ............................ 600/3 |
| 6,597,762 B1 | 7/2003 | Ferrant et al. |
| 6,605,030 B2 | 8/2003 | Weinberger |
| 6,607,477 B1 | 8/2003 | Longton et al. |
| 6,610,013 B1 | 8/2003 | Fenster et al. |
| 6,611,575 B1 | 8/2003 | Alyassin et al. |
| 6,615,070 B2 | 9/2003 | Lee |
| 6,616,629 B1 | 9/2003 | Verin et al. |
| 6,620,111 B2 | 9/2003 | Stephens et al. |
| 6,626,849 B2 | 9/2003 | Huitema et al. |
| 6,633,674 B1 | 10/2003 | Gemperline et al. |
| 6,638,235 B2 | 10/2003 | Miller et al. |
| 6,647,092 B2 | 11/2003 | Eberhard et al. |
| 6,652,441 B2 | 11/2003 | Weinberger et al. |
| 6,673,006 B2 | 1/2004 | Winkler |
| 6,685,618 B2 | 2/2004 | Tam et al. |
| 6,706,014 B2 | 3/2004 | Banik et al. |
| 6,723,052 B2 | 4/2004 | Mills |
| 6,744,848 B2 | 6/2004 | Stanton et al. |
| 6,746,392 B2 | 6/2004 | Stiger et al. |
| 6,748,044 B2 | 6/2004 | Sabol et al. |
| 6,749,555 B1 | 6/2004 | Winkler et al. |
| 6,749,595 B1 | 6/2004 | Murphy |
| 6,751,285 B2 | 6/2004 | Eberhard et al. |
| 6,752,752 B2 | 6/2004 | Geitz |
| 6,758,824 B1 | 7/2004 | Miller et al. |
| 6,770,058 B1 | 8/2004 | Liprie |
| 6,813,334 B2 | 11/2004 | Koppe et al. |
| 6,882,700 B2 | 4/2005 | Wang et al. |
| 6,885,724 B2 | 4/2005 | Li et al. |
| 6,912,319 B1 | 6/2005 | Barnes et al. |
| 6,913,600 B2 | 7/2005 | Valley et al. |
| 6,923,754 B2 | 8/2005 | Lubock |
| 6,940,943 B2 | 9/2005 | Claus et al. |
| 6,955,641 B2 | 10/2005 | Lubock |
| 6,970,531 B2 | 11/2005 | Eberhard et al. |
| 6,978,040 B2 | 12/2005 | Berestov |
| 6,983,754 B1 | 1/2006 | Anderson et al. |
| 6,987,831 B2 | 1/2006 | Ning |
| 6,999,554 B2 | 2/2006 | Mertelmeier |
| 7,098,463 B2 | 8/2006 | Adamovics |
| 7,107,089 B2 | 9/2006 | Lee |
| 7,110,490 B2 | 9/2006 | Eberhard et al. |
| 7,110,502 B2 | 9/2006 | Tsuji |
| 7,123,684 B2 | 10/2006 | Jing et al. |
| 7,127,091 B2 | 10/2006 | Op De Beek et al. |
| 7,142,633 B2 | 11/2006 | Eberhard et al. |
| 7,171,255 B2 | 1/2007 | Holupka et al. |
| 7,201,715 B2 | 4/2007 | Burdette et al. |
| 7,214,178 B2 | 5/2007 | Lubock |
| 7,245,694 B2 | 7/2007 | Jing et al. |
| 7,315,607 B2 | 1/2008 | Ramsauer |
| 7,319,735 B2 | 1/2008 | Defreitas et al. |
| 7,322,929 B2 | 1/2008 | Lovoi |
| 7,323,692 B2 | 1/2008 | Rowlands et al. |
| 7,404,791 B2 | 7/2008 | Linares et al. |
| 7,407,476 B2 | 8/2008 | Lubock et al. |
| 7,413,539 B2 | 8/2008 | Lubock et al. |
| 7,430,272 B2 | 9/2008 | Jing et al. |
| 7,443,949 B2 | 10/2008 | Defreitas et al. |
| 7,465,268 B2 | 12/2008 | Lubock et al. |
| 7,476,235 B2 | 1/2009 | Diederich et al. |
| 7,497,819 B2 | 3/2009 | White et al. |
| 7,497,820 B2 | 3/2009 | White et al. |
| 7,513,861 B2 | 4/2009 | Klein et al. |
| 7,517,310 B2 | 4/2009 | Lubock et al. |
| 7,609,806 B2 | 10/2009 | Defreitas et al. |
| 7,630,533 B2 | 12/2009 | Ruth et al. |
| 7,662,082 B2 | 2/2010 | White et al. |
| 7,697,660 B2 | 4/2010 | Ning |
| 7,783,006 B2 | 8/2010 | Stewart et al. |
| 7,792,245 B2 | 9/2010 | Hitzke et al. |
| 7,869,563 B2 | 1/2011 | Defreitas et al. |
| 7,885,382 B2 | 2/2011 | Stewart et al. |
| 7,887,476 B2 | 2/2011 | Hermann et al. |
| 7,955,246 B2 | 6/2011 | Lubock et al. |
| 8,075,469 B2 | 12/2011 | Lubock et al. |
| 8,079,946 B2 | 12/2011 | Lubock et al. |
| 8,123,722 B2 | 2/2012 | Chang et al. |
| 8,137,256 B2 * | 3/2012 | Cutrer et al. ..................... 600/3 |
| 8,192,344 B2 | 6/2012 | Lubock et al. |
| 8,277,370 B2 * | 10/2012 | Quick ............... 600/3 |
| 8,287,442 B2 | 10/2012 | Quick |
| 8,565,374 B2 | 10/2013 | Defreitas et al. |
| 9,352,172 B2 | 5/2016 | Benson |
| 9,623,260 B2 | 4/2017 | White |
| 2001/0016725 A1 | 8/2001 | Valley et al. |
| 2001/0038681 A1 | 11/2001 | Stanton et al. |
| 2001/0038861 A1 | 11/2001 | Hsu et al. |
| 2001/0049464 A1 | 12/2001 | Ganz |
| 2001/0051669 A1 | 12/2001 | McGhee |
| 2002/0012450 A1 | 1/2002 | Tsujii |
| 2002/0026090 A1 | 2/2002 | Kaplan et al. |
| 2002/0045893 A1 | 4/2002 | Lane et al. |
| 2002/0050986 A1 | 5/2002 | Inouc et al. |
| 2002/0055666 A1 | 5/2002 | Hunter et al. |
| 2002/0075997 A1 | 6/2002 | Unger et al. |
| 2002/0095114 A1 | 7/2002 | Palasis |
| 2002/0156342 A1 | 10/2002 | Burton et al. |
| 2002/0177804 A1 | 11/2002 | Saab |
| 2002/0177870 A1 | 11/2002 | Sepetka |
| 2003/0018272 A1 | 1/2003 | Treado et al. |
| 2003/0073895 A1 | 4/2003 | Nields et al. |
| 2003/0095624 A1 | 5/2003 | Eberhard et al. |
| 2003/0144570 A1 | 7/2003 | Hunter et al. |
| 2003/0153803 A1 | 8/2003 | Harmon |
| 2003/0191491 A1 | 10/2003 | Duane et al. |
| 2003/0194050 A1 | 10/2003 | Eberhard et al. |
| 2003/0194051 A1 | 10/2003 | Wang et al. |
| 2003/0194121 A1 | 10/2003 | Eberhard et al. |
| 2003/0210254 A1 | 11/2003 | Doan et al. |
| 2003/0215120 A1 | 11/2003 | Uppaluri et al. |
| 2004/0015193 A1 | 1/2004 | Lamson |
| 2004/0039437 A1 | 2/2004 | Sparer et al. |
| 2004/0054366 A1 | 3/2004 | Davison et al. |
| 2004/0066884 A1 | 4/2004 | Hermann Claus et al. |
| 2004/0066904 A1 | 4/2004 | Eberhard et al. |
| 2004/0087827 A1 | 5/2004 | Lubock |
| 2004/0094167 A1 | 5/2004 | Brady et al. |

(56) References Cited

U.S. PATENT DOCUMENTS

| | | |
|---|---|---|
| 2004/0101095 A1 | 5/2004 | Jing et al. |
| 2004/0109529 A1 | 6/2004 | Eberhard et al. |
| 2004/0116767 A1 | 6/2004 | Lebovic et al. |
| 2004/0147800 A1 | 7/2004 | Barber et al. |
| 2004/0171986 A1 | 9/2004 | Tremaglio, Jr. et al. |
| 2004/0215048 A1 | 10/2004 | Lubock |
| 2004/0260142 A1 | 12/2004 | Lovoi |
| 2004/0267157 A1 | 12/2004 | Miller et al. |
| 2005/0016771 A1 | 1/2005 | Mayes et al. |
| 2005/0049521 A1 | 3/2005 | Miller et al. |
| 2005/0059990 A1 | 3/2005 | Ayala et al. |
| 2005/0061771 A1 | 3/2005 | Murphy |
| 2005/0063509 A1 | 3/2005 | DeFreitas et al. |
| 2005/0078797 A1 | 4/2005 | Danielsson et al. |
| 2005/0080313 A1 | 4/2005 | Stewart et al. |
| 2005/0101823 A1 | 5/2005 | Linares et al. |
| 2005/0105679 A1 | 5/2005 | Wu et al. |
| 2005/0113681 A1 | 5/2005 | DeFreitas |
| 2005/0113715 A1 | 5/2005 | Schwindt et al. |
| 2005/0124843 A1 | 6/2005 | Singh |
| 2005/0129172 A1 | 6/2005 | Mertelmeier |
| 2005/0135555 A1 | 6/2005 | Claus et al. |
| 2005/0135664 A1 | 6/2005 | Kaufhold et al. |
| 2005/0182286 A1 | 8/2005 | Lubock |
| 2005/0226375 A1 | 10/2005 | Eberhard et al. |
| 2005/0240073 A1 | 10/2005 | Apffelstaedt et al. |
| 2005/0240074 A1 | 10/2005 | Lubock |
| 2005/0267320 A1 | 12/2005 | Barber et al. |
| 2005/0277577 A1 | 12/2005 | Hunter et al. |
| 2006/0014997 A1* | 1/2006 | Kindlein et al. .............. 600/3 |
| 2006/0020156 A1 | 1/2006 | Shukla |
| 2006/0020256 A1 | 1/2006 | Bell et al. |
| 2006/0030784 A1 | 2/2006 | Miller et al. |
| 2006/0074288 A1 | 4/2006 | Kelly |
| 2006/0098855 A1 | 5/2006 | Gkanatsios |
| 2006/0100475 A1 | 5/2006 | White et al. |
| 2006/0116546 A1 | 6/2006 | Eng |
| 2006/0129062 A1 | 6/2006 | Nicoson et al. |
| 2006/0136051 A1 | 6/2006 | Furst et al. |
| 2006/0149186 A1 | 7/2006 | Wantink |
| 2006/0155209 A1 | 7/2006 | Miller et al. |
| 2006/0167416 A1 | 7/2006 | Mathis et al. |
| 2006/0173233 A1 | 8/2006 | Lovoi |
| 2006/0173235 A1 | 8/2006 | Lim et al. |
| 2006/0205992 A1 | 9/2006 | Lubock et al. |
| 2006/0291618 A1 | 12/2006 | Eberhard et al. |
| 2007/0005003 A1 | 1/2007 | Patterson et al. |
| 2007/0030949 A1 | 2/2007 | Jing et al. |
| 2007/0036265 A1 | 2/2007 | Jing et al. |
| 2007/0055144 A1 | 3/2007 | Neustadter et al. |
| 2007/0076844 A1 | 4/2007 | Defreitas et al. |
| 2007/0106108 A1 | 5/2007 | Hermann et al. |
| 2007/0142694 A1 | 6/2007 | Cutrer et al. |
| 2007/0142779 A1 | 6/2007 | Duane et al. |
| 2007/0167665 A1 | 7/2007 | Hermann et al. |
| 2007/0167666 A1 | 7/2007 | Lubock et al. |
| 2007/0191667 A1 | 8/2007 | Lubock et al. |
| 2007/0223651 A1 | 9/2007 | Wagenaar et al. |
| 2007/0225600 A1 | 9/2007 | Weibrecht |
| 2007/0242800 A1 | 10/2007 | Jing |
| 2007/0270627 A1 | 11/2007 | Cutrer et al. |
| 2008/0009659 A1 | 1/2008 | Smith et al. |
| 2008/0019581 A1 | 1/2008 | Gkanatsios |
| 2008/0045833 A1 | 2/2008 | Defreitas |
| 2008/0057298 A1 | 3/2008 | Finley |
| 2008/0064915 A1 | 3/2008 | Lubock |
| 2008/0071212 A1 | 3/2008 | Lubock et al. |
| 2008/0086083 A1 | 4/2008 | Towler |
| 2008/0091055 A1 | 4/2008 | Nguyen et al. |
| 2008/0101537 A1 | 5/2008 | Sendai |
| 2008/0112534 A1 | 5/2008 | DeFreitas et al. |
| 2008/0130979 A1 | 6/2008 | Ren |
| 2008/0177127 A1 | 7/2008 | Allan et al. |
| 2008/0188705 A1 | 8/2008 | Lubock et al. |
| 2008/0221384 A1 | 9/2008 | Chi Sing et al. |
| 2008/0221444 A1 | 9/2008 | Ritchie et al. |
| 2008/0228023 A1 | 9/2008 | Jones et al. |
| 2008/0228024 A1 | 9/2008 | Jones et al. |
| 2008/0228025 A1 | 9/2008 | Quick |
| 2008/0228150 A1 | 9/2008 | Jones et al. |
| 2008/0281142 A1 | 11/2008 | Lubock et al. |
| 2008/0281143 A1 | 11/2008 | Lubock et al. |
| 2008/0287801 A1 | 11/2008 | Magnin et al. |
| 2009/0003519 A1 | 1/2009 | Defreitas |
| 2009/0010384 A1 | 1/2009 | Jing |
| 2009/0030259 A1 | 1/2009 | Quick |
| 2009/0080594 A1 | 3/2009 | Brooks |
| 2009/0080602 A1 | 3/2009 | Brooks |
| 2009/0093821 A1 | 4/2009 | Edmundson |
| 2009/0124845 A1 | 5/2009 | Lubock et al. |
| 2009/0135997 A1 | 5/2009 | Defreitas |
| 2009/0156880 A1 | 6/2009 | Allan et al. |
| 2009/0156882 A1 | 6/2009 | Chi Sing et al. |
| 2009/0171157 A1 | 7/2009 | Diedrich et al. |
| 2009/0188098 A1 | 7/2009 | Acosta et al. |
| 2009/0198095 A1 | 8/2009 | Acosta et al. |
| 2009/0213987 A1 | 8/2009 | Stein et al. |
| 2009/0268865 A1 | 10/2009 | Ren |
| 2009/0296882 A1 | 12/2009 | Gkanatsios |
| 2009/0304147 A1 | 12/2009 | Jing et al. |
| 2010/0048977 A1 | 2/2010 | Sing et al. |
| 2010/0054400 A1 | 3/2010 | Ren |
| 2010/0069878 A1* | 3/2010 | Parsai ............... A61M 25/1002 604/500 |
| 2010/0086188 A1 | 4/2010 | Ruth |
| 2010/0150306 A1 | 6/2010 | Defreitas et al. |
| 2010/0195882 A1 | 8/2010 | Ren |
| 2010/0204534 A1 | 8/2010 | Damarati |
| 2010/0204535 A1 | 8/2010 | Damarati |
| 2010/0226475 A1 | 9/2010 | Smith |
| 2010/0268029 A1 | 10/2010 | Phan |
| 2010/0290585 A1 | 11/2010 | Eliasson |
| 2011/0069809 A1 | 3/2011 | Defreitas et al. |
| 2012/0046647 A1 | 2/2012 | Matsukurna et al. |
| 2012/0071705 A1 | 3/2012 | Lubock et al. |
| 2012/0088952 A1 | 4/2012 | Lubock et al. |
| 2012/0178983 A1 | 7/2012 | Benson |
| 2013/0225902 A1 | 8/2013 | White |
| 2016/0287902 A1 | 10/2016 | Benson |
| 2017/0080252 A1 | 3/2017 | Lubock et al. |

FOREIGN PATENT DOCUMENTS

| | | |
|---|---|---|
| EP | 0536440 | 4/1993 |
| EP | 0642766 | 3/1995 |
| EP | 0693293 | 1/1996 |
| EP | 0719571 | 7/1996 |
| EP | 775467 | 5/1997 |
| EP | 0853957 | 7/1998 |
| EP | 0 867 200 | 9/1998 |
| EP | 0982001 | 3/2000 |
| EP | 1051990 | 11/2000 |
| EP | 1070514 | 1/2001 |
| EP | 1402922 | 3/2004 |
| EP | 1428473 | 6/2004 |
| EP | 1541188 | 6/2005 |
| EP | 1618924 | 1/2006 |
| EP | 1759637 | 3/2007 |
| JP | 10137250 | 5/1998 |
| JP | 2001120561 | 5/2001 |
| RU | 2177350 | 12/2001 |
| WO | WO 90/05485 | 5/1990 |
| WO | WO92/10932 | 7/1992 |
| WO | WO93/09724 | 5/1993 |
| WO | WO 9520241 | 7/1995 |
| WO | WO 9712540 | 4/1997 |
| WO | WO97/19723 | 6/1997 |
| WO | WO 97/45053 | 12/1997 |
| WO | WO 98/16903 | 4/1998 |
| WO | WO 9815315 | 4/1998 |
| WO | WO99/11325 | 3/1999 |
| WO | WO99/33515 | 7/1999 |
| WO | WO 9934869 | 7/1999 |
| WO | WO99/42163 | 9/1999 |

(56) References Cited

FOREIGN PATENT DOCUMENTS

| WO | WO 01/14011 | 7/2000 |
|---|---|---|
| WO | WO 00/51484 | 9/2000 |
| WO | WO 01/43826 | 6/2001 |
| WO | WO 01/58346 | 8/2001 |
| WO | WO 02/09599 | 2/2002 |
| WO | WO 02/069862 | 9/2002 |
| WO | WO 03/020114 | 3/2003 |
| WO | WO 2004/043531 | 5/2004 |
| WO | WO 2004/043535 | 5/2004 |
| WO | WO 2005/037363 | 4/2005 |
| WO | WO 2005039655 | 5/2005 |
| WO | WO 2005039665 | 5/2005 |
| WO | WO 2005/051197 | 6/2005 |
| WO | WO 2005/067442 | 7/2005 |
| WO | WO 2005110230 | 11/2005 |
| WO | WO 2005112767 | 12/2005 |
| WO | WO 2006/055830 | 5/2006 |
| WO | WO 2006/058160 | 6/2006 |
| WO | WO 2007/027831 | 3/2007 |
| WO | WO 2007/143560 | 12/2007 |
| WO | WO08/067557 | 6/2008 |
| WO | WO09/79170 | 6/2009 |

OTHER PUBLICATIONS

Nath, Ph.D. et al., Development of an 241 Am Applicator for Intracavitary Irradiation of Gynecologic Cancers, I.J. Radiation Oncology Biol. Phys., May 1988, vol. 14, p. 969-978.
International Search Report and Written Opinion from related PCT Application No. PCT/US2010/023454 dated May 7, 2010.
International Search Report and Written Opinion from related PCT Application No. PCT/US2010/023461 dated Jun. 1, 2010.
International Search Report and Written Opinion from related PCT Application No. PCT/US2010/033370 dated Jul. 30, 2010.
International Search Report and Written Opinion from related PCT Application No. PCT/US2010/033373 dated Aug. 9, 2010.
"Essentials for life: Senographe Essential Full-Field Digital Mammography system", GE Health-care Brochure, MM-0132-05.06-EN-US, 2006, 12 pgs.
"Filtered Back Projection," (NYGREN) published May 8, 2007; URL:http://web.archive.org/web/19991010131715/http://www.owlnet.rice.edu/-.about.e1ec539/Projects97/cult/node2.html, 2 pgs.
"Lorad Selenia" Document B-BI-SEO US/Intl (May 2006), copyright Hologic 2006, 12 pgs.
"Variable shield for radiation-therapy sourcewire and centering catheter", Research disclosure, Mason Publications, Hampshire, GB, vol. 438, No. 48, Oct. 2000, XP007126916, 1 page.
Abstracts of the 11th International Conference on Brain tumor Research and Therapy Oct. 31-Nov. 3, 1995, Silverado Country Club and Resort, Napa, California, Journal of Neuro-Oncology 28, p. 72, 1996, 2 pages all together.
Akagi, Y, et al.,"Optimum Fractionation for High-Dose-Rate Endoesophageal Brachytherapy Following External Irradiation of Early State Esophageal Cancer", Int. J. Radiation Oncology Biol. Phys., vol. 43, 1999, pp. 525-530, Elsevier Science, Inc.
Astrahan, Melvin A., PhD et al., "Optimization of Mammosite therapy", Int. J. Radiation Oncology Biol. Phys, vol. 58, No. 1, pp. 220-232, 2004.
Bowsher. W. G., et al., "Update on Urology-Prostate Cancer. 4-Treatment of Local Disease". European Journal of Surgical Oncology. 1995 pp. 679-682. vol. 21. No. 6.
Chan, Heang-Ping et al., "ROC study of the effect of stereoscopic imaging on assessment of breast lesions", Medica Physics, vol. 32, No. 4, Apr. 2005, 7 pgs.
Cole, Elodia, et al., "The Effects of Gray Scale Image Processing on Digital Mammography Interpretation Performance", Academic Radiology, vol. 12, No. 5, pp. 585-595, May 2005.
Cuttino, L. W., et al.,"CT-Guided Multi-Catheter Insertion Technique for Partial Breast Brachytherapy: Reliable Target Coverage and Dose Homogeneity", Brachy1herapy 4, 2005, pp. 10-17, Elsevier.

Das, R. K., et al., "3D-CT-Based High-Dose-Rate Breast Brachytherapy Implants: Treatment Planning and Quality Assurance", Int. J. Radiation Oncology Biol. Phys. 2004, pp. 1224-1228, vol. 59, No. 4, Elsevier Inc.
Debicki, M. P., et al., "Localized Current Field Hyperthermia in Carcinoma of The Cervix: 3-D Computer Simulation of SAR Distribution". International Journal of Hyperthermia. 1999. pp. 427-440. vol. 15. No. 5.
Demanes, D. J . et al., "The Use and Advantages of a Multichannel Vaginal Cylinder in High-Dose-Rate Brachytherapy". Int. J. Radiation Oncology Biol. Phys. (1999). pp. 211-219. vol. 44. No. 1. Elsevier Science Inc.
Dempsey, J. F. et al., "Dosimetric Properties of a Novel Brachytherapy Balloon Applicator for The Treatment of Malignant Brain-Tumor Resection-Cavity Margins", Int. J. Radiation Oncology Biol. Phys., May 1998, pp. 421-429. vol. 42. No. 2. Elsevier.
Devic et al., "Advantages of Inflatable Multichannel Endorectal Applicator in The Neo-Adjuvant Treatment of Patients With Locally Advanced Rectal Cancer With HOR Brachytherapy", Journal of Applied Clinical Medical Physics, Spring 2005, pp. 44-49, vol. 6, No. 2.
Digital Clinical Reports, Tomosynthesis, GE Brochure 98-5493, Nov. 1998, 8 pgs.
Edmundson,Gregory K. et al., "Dosimetric Characteristics of the Mammosite RTS, a New Breast Brachytherapy Applicator", Int. J. Radiation Oncology Biol. Phys, vol. 52, No. 4, pp. 1132-1139, 2002.
Federica Pediconi et al., "Color-coded automated signal intensity-curve for detection and characterization of breast lesions: Preliminary evaluation of a new software for MR-based breast imaging", International Congress Series 1281 (2005) 1081-1086.
Fowler, J. E., "Brief Summary of Radiobiological Principles in Fractionated Radiotherapy", Seminars in Radiation Oncology, Jan. 1992, pp. 16-21, vol. 2, No. 1, W. B. Saunders Company.
Friedman, M, et al., "A New Technic for the Radium Treatment of Carcinoma of The Bladder", Presented at the Thirty-fourth Annual Meeting of the Radiological Society of North America, Dec. 5-10, 1948, pp. 342-362.
Friedman, M, et al., "Irradiation of Carcinoma of The Bladder by a Central Intracavitary Radium or Cobalt 60 Source (The Walter Reed Technique)", Presented at the Annual Meeting of the American Radium Society, 1955, pp. 6-31.
Garipagaoglu, M. et al., "Geometric and Dosimetric Variations of ICRU Bladder and Rectum Reference Points in Vaginal Cuff Brachytherapy Using Ovoids", Int. J. Radiation Oncology Biol. Phys. 2004, pp. 1607-1615. Elsevier Inc.
Gaspar, L. E., et al., "Esophageal Brachytherapy", Principles and Practice of Brachytherapy, 1997, pp. 305-321, Futrua Publishing Company, Inc., Armouk, New York.
Glasgow, G. P., et al. "Remote Afterloading Technology", AAPM Report No. 41, 1993, pp. i-vi and 1-107, American Institute of Physics, Inc., 116 pgs.
Gutin, P.H. et al., "A coaxial catheter system for afterloading radioactive sources for the interstitial irradiation of brain tumors", J. Neurosur, vol. 56, pp. 734-735, 1982.
Hall, J. W., et al., "Histologic Changes in Squamous-Cell Carcinoma of the Mouth and Oropharynx Produced by Fractionated External Roentgen Irradiation", Radiological Society of North America, 1948, pp. 318-350, Mar. 3, 1950.
Harada, T, et al.,"Transcystoscopic Intracavitary irradiation for Carcinoma of the Bladder: Technique and Preliminary Clinical Results", The Journal of Urology, Oct. 1987, pp. 771-774, vol. 138, No. 4, The Williams & Wilkins Co.
Harper, Paul V., "Some Therapeutic Applications of Radioisotopes", Journal of the Mississippi State Medical Association, Oct. 1966, vol. VII, pp. 526-533.
Hewitt, C. B., et al., "Intracavitary Radiation in the Treatment of Bladder Tumors", The Journal of Urology, vol. 107, Apr. 1972, pp. 603-606, The Williams & Wilkins Co.
Hewitt, C. B., et al., "Update on Intracavitary Radiation in The Treatment of Bladder Tumors", The Journal of Urology; Official Journal of the American Urological Association, Inc., 1981, pp. 323-325, vol. 126 Sep., the Williams & Wilkins Co.

(56) References Cited

OTHER PUBLICATIONS

Hieshima, G. B., et al. "A Detachable Balloon for Therapeutic Transcatheter Occlusions 1", Technical Notes, Jan. 1981, pp. 227-228, vol. 138.
Hine, G. J., et al., "Isodose Measurements of Linear Radium Sources in Air and Water by Means of an Automatic Isodose Recorder", The American Journal of Roentgenology and Radium Therapy, 1950, pp. 989-998, vol. 64, No. 6, The Societies.
Hoshino, T., "Brain Tumor Research Center", Abstracts of the 11th Conference on Brain Tumor Research and Therapy, Journal of Neuro-Oncology 28, 1996, pp. 31-113.
Johannesen, T.B. et al, "Intracavity Fractioned Balloon Brachytherapy in Glioblastoma", Acta Neurochir (Wien) (1999) 141: 127-133.
Kaufman, N., "Remote Afterloading Intraluminal Brachytherapy in The Treatment of Rectal, Rectosigmoid, and Anal Cancer: A Feasibility Study", International Journal of Radiation Oncology, Biology, Physics, Sep. 1989, pp. 663-668, vol. 17, Issue 3, Pergamon Press pic.
Kita et al., "Correspondence between different view breast X-rays using simulation of breast deformation", Proceedings 1998 IEE Computer Society Conference on Computer Vision and Pattern Recognition, Santa Barbara, CA, Jun. 23-25, 1998, pp. 700-707.
Kolotas, C. et al., "CT Guided Interstitial High Dose Rate Brachytherapy for Recurrent Malignant Gliomas". The British Journal of Radiology. 72. (1999), pp. 805-808.
Kuettel, M. R. et al.. "Treatment of Female Urethral Carcinoma in Medically Inoperable Patients Using External Beam Irradiation and High Dose Rate Intracavitary Brachytherapy", The Journal of Urology. May 1997, pp. 1669-1671. vol. 157. The American Urological Association. Inc.
Lewis, J, et al., "Intracranial Brachytherapy Using a High Dose Rate Microselectron", Northern Centre for Cancer Treatment, Dept. of Neurosciences, Regional Medical Physics Department, Newcastle.
Low-Beer, B. V. A., "Radioisotope Therapy", "The Clinical Use of Radioactive Isotopes", 1950, pp. 284-349, Charles C. Thomas, Publisher, Springfield, Illinois, U.S.A., See pp. 343-349.
Low-Beer, B. V. A., "The Therapeutic Use of Radioactive Isotopes", "Practical Therapeutics", Dec. 1954, pp. 69-87, vol. X, No. 6.
Mammographic Accreditation Phantom, http://www.cirsinc.com/pdfs/015cp.pdf, (2006), 2 pgs.
Marshall V. F., et al., "Current Clinical Problems Regarding Bladder Tumors", Symposium on Bladder Tumors, 1956, pp. 543-550, 9/3/May-Jun., J.B. Lippincott Co, Etc.
Micheletti, E., et al., "High-Dose-Rate Brachytherapy for Poor-Prognosis, High-Grade Glioma: (Phase II) Preliminary Results", Tumori, 1996, pp. 339-344.
Muller, J. H., "Radiotherapy of Bladder Cancer by Means of Rubber Balloons Filled In Situ With solutions of A Radioactive Isotope (Co60)", Cancer, A Journal of the American Cancer Society, Jul.-Aug. 1955, pp. 1035-1043, vol. 8, No. 4, J.B. Lippincott Company, Philidelphia.
Nag, S, "Modern Techniques of Radiation Therapy for Endometrial Cancer", Clinical Obstetrics and Gynecology, Sep. 1996, pp. 728-744, vol. 39, No. 3, Lippincott-Raven Publishers.
Nag, S., et al., "Perineal Template Interstitial Barchytherapy Salvage for Recurrent Endometrial Adenocarcinoma Metastatic to the Vagina", Necologic Oncology 66, 1997, pp. 16-19, Article No. G0974722, Academic Press.
Nag, S., et al., "Remote Controlled High Dose Rate Brachytherapy", Critical Reviews in Oncology/Hematology 22, 1996, pp. 127-150, Elsevier Science Ireland Ltd.
Nag, S., et al., "The Future of High Dose Rate Brachytherapy", High Dose Rate Brachytherapy: A Textbook, 1994, pp. 447-453, Futura Publishing Company, Inc., Armonk, New York 10504.
Pernot, M., "Combined Surgery and Brachytherapy in the Treatment of Some Cancers of the Bladder (Partial Cystectomy and Interstitial Iridium—192)", Radiotherapy & Oncology, 1996, pp. 115-120, Elsevier Science Ireland Ltd.
Rotman, M., et al., "The Intracavitary Applicator in Relation to Complications of Pelvic Radiation-The Ernst System", Int. J. Radiation Oncology Biol. Phys., 1978, pp. 951-956, vol. 4, Pergamon Press Inc.
Russel, A.H., et al, "Intracavitary Irradiation for Carcinoma of the Urinary Bladder: Rationale, Technique, and Preliminary Results", Int. J. Radiation Oncology. Phys., 1984, pp. 215-219, vol. 10, Pergamon Press Ltd.
Senographe 700 & 800T (GE); 2-page download on Jun. 22, 2006 from www.gehealthcare.com/inen/rad/whe/products/mswh800t.html.; Figures 1-7 on 4 sheets re lateral shift compression paddle, 2 pgs.
Slevin. N. J. et al., "Intracavitary Radiotherapy Boosting for Nasopharynx Cancer", The British Journal of Radiology. 70. Apr. 1997, pp. 412-414.
Smith, A., "Fundamentals of Breast Tomosynthesis", White Paper, Hologic Inc., WP-00007, Jun. 2008, 8 pgs.
Sneed. P. K. et al., "Interstitial Brachytherapy Procedures for Brain Tumors", Seminars in Surgical Oncology 1997; 13: 157-166. Wiley-Liss. Inc.
Stubbs, J.B., et al., "Preclinical Evaluation of a Novel Device for Delivering Brachytherapy to the Margins of Resected Brain Tumor Cavities", J. Neurosurg 96, Feb. 2002, pp. 335-343, vol. 96.
Sylvester. J., et al., "Interstitial Implantation Techniques in Prostate Cancer", Journal of Surgical Oncology 1997; 66: 65-75. Wiley-Liss. Inc.
Symon et al., "Individual Fraction Optimization vs. First Fraction Optimization for Multichannel Applicator Vaginal Cuff High-Dose-Rate Brachytherapy", pp. 211-215, Brachytherapy 5 (2006), Elsevier.
Tan, L. T. et al., "Radical Radiotherapy for Carcinoma of the Uterine Cervix Using External Beam Radiotherapy and A Single Line Source Brachytherapy Technique: The Clatterbridge Technique", The British Journal of Radiology. 70. date Dec. 1997, pp. 1252-1258.
Tanderup et al. "Multi-Channel Intracavitary Vaginal Brachytherapy Using Three-Dimensional Optimization of Source Geometry", Radiation & Oncology Journal of the European Society for Therapeutic Radiology and Oncology, 2004, pp. 81-85, Radiotherapy and Oncology 70 (2004), Elsevier Ireland Ltd.
Vicini, F. A., et al, "Dose-Volume Analysis for Quality Assurance of Interstitial Brachytherapy for Breast Cancer", Int. J. Radiation Oncology Biol. Phys., vol. 45, 1999, pp. 803-810, Elsevier Science Inc.
Voung, T, et al., "High-Dose-Rate Endorectal Brachytherapy in the Treatment of Loacally Advanced Rectal Carcinoma: Technical Aspects", Brachytherapy 4, 2005, pp. 230-235, Elsevier.
Walton, R. J., "Therapeutic Uses of Radioactive Isotopes in the Royal Cancer Hospital", The British Journal of Radiology, 1950, pp. 559-599, William Heinemann, Publisher.
Walton, R. J., et al., Radioactive Solution (24Na and 82 Br) in the Treatment of Carcinoma of The Bladder:, British Medical Bulletin, 1952, pp. 158-165, Medical Dept., The British Council.
Wang, C. C., "Carcinoma of the Nasopharynx", Radiation Therapy of Head and Neck Neoplasms, 1997, pp. 257-280, Chapter 10, Wiley-Liss, Inc.
Wheeler, F.W. et al. (2006), "Micro-Calcification Detection in Digital Tomosynthesis Mammography", Proceedings of SPIE, Conf-Physics of Semiconductor Devices, Dec. 11, 2001 to Dec. 15, 2001, Delhi, SPIE, US, vol. 6144, Feb. 13, 2006, 12 pgs.
Wolf, C. D., et al., "A Unique Nasopharynx Brachytherapy Technique", Official Journal of the American Association of Medical Dosimetrists, 1990, pp. 133-136, vol. 15, Issue No. 3., Pergamon Press.
Wu, Tao et al., "Tomographic mammography using a limited number of low-dose cone-beam images", Medical Physics, AIP, Melville, NY, vol. 30, No. 3, Mar. 1, 2003, pp. 365-380.
"DuPont Teflon PFA HP Plus", XP007904995, retrieved from the internet: URL: http://www2.dupont.com/Teflon_Industrial/en_US/assets/downloads/ h88800.pdf; retrieved on Jun. 19, 2008, by Authorized Officer in International Application PCT/US2008/003364, 4 pgs.

(56) References Cited

OTHER PUBLICATIONS

Xu, Z., et al., "Calculation of Dose Distribution Near an Innovative Concentric Balloon Catheter for Endovascular Brachytherapy", Cardiovascular Radiation Medicine 2, 2000, pp. 26-31, Elsevier Science Inc.

Yin, W., "Brachtherapy of Carcinoma of the Esophagus in China, 1970-1974 and 1982-1984", Brachytherapy HOR and LOR, May 4-6, 1989, pp. 52-56.

Lewis, J, et al., "Intracranial Brachytherapy Using a High Dose Rate Microselectron", Northern Centre for Cancer Treatment, Dept. of Neurosciences, Regional Medical Physics Department, Newcastle General Hospital, Newcastle Upon Tyne, UK, Radiation and Oncology, vol. 39, Supplement 1, May 1996, pp. 45-45, 1 page, p. 179.

\* cited by examiner

FIG. 7

LUMEN VISUALIZATION AND IDENTIFICATION SYSTEM FOR MULTI-LUMEN BALLOON CATHETER

FIELD OF THE INVENTION

This invention relates generally to methods and apparatus for treating proliferative tissue disorders using a multi-lumen brachytherapy device and more particularly to a system for visually distinguishing the lumens of the multi-lumen device.

BACKGROUND

Malignant tumors are often treated by surgical resection of the tumor to remove as much of the tumor as possible. Infiltration of the tumor cells into normal tissue surrounding the tumor, however, can limit the therapeutic value of surgical resection because the infiltration can be difficult or impossible to treat surgically. Radiation therapy can be used to supplement surgical resection by targeting the residual tumor margin after resection, with the goal of reducing its size or stabilizing it.

Radiation therapy can be administered through one of several methods, or a combination of methods, including external-beam radiation, stereotactic radiosurgery, and permanent or temporary brachytherapy. The term "brachytherapy," as used herein, refers to radiation therapy delivered by a source of therapeutic rays inserted into the body at or near a tumor or other proliferative tissue disease site.

One interstitial brachytherapy therapy system is the Mammosite® system, provided by Hologic, Inc. of Bedford, Mass. The MammoSite system includes a catheter shaft with an inflatable balloon mounted on its distal end. A lumen extends within the catheter shaft, into the balloon. The catheter shaft is inserted into a body so that the balloon is positioned within a resected cavity. The balloon is subsequently inflated and radioactive material, for example in the form of one or more radioactive seeds, is loaded into the lumen for radiation delivery.

Mammosite® is a single lumen brachytherapy catheter. In single lumen brachytherapy catheters, the lumen is generally centered within the balloon such that the balloon generates isodose profiles in the target tissue that are substantially symmetrical, similar in shape to the inflated balloon. However, symmetric dosing may not always be desirable, as the resection cavity may not be uniform or regular in shape and size. Asymmetric dosing methods, such as those described in U.S. Pat. No. 6,749,595 include catheters with multiple lumens, where radioactive seeds may be placed within the different lumens to achieve different dosing profiles. Methods and systems for using multiple lumens for interstitial breast brachytherapy are also described by Lubbock in U.S. Patent application publication number 20070167667, Cutrer in U.S. Patent application publication number 20070142694 and Damarati in U.S. patent Ser. No. 12/369,214.

One problem with existing multi-lumen designs is that it is often difficult to visually distinguish the lumens and identify their end point locations once the device is implanted into the patient. Clearly visualizing the individual lumens in a multi-lumen brachytherapy balloon catheter is perceived as a development challenge to overcome. Radiation oncologists and physicists must be able to distinguish and identify individual lumens on a computer tomography (CT) scan that is imported into dosimetry planning software. Limitations of CT scan technology, proximity of multiple lumens to each other and limitations on the ease of manipulating scans within various dosimetry planning systems all present challenges to adequate lumen visualization and identification.

One current method for visualizing and identifying lumens includes inserting customized, dummy guidewires into the lumens to identify lumens and visualize the end of each lumen. The configurations consist of a plastic tube in which small pieces of wire are embedded at the tip and then in different staggered patterns such that a unique wire can be used in each lumen. Customization of guidewires, however, increases the overall cost of the multi-lumen device.

Commercially available standard dummy guidewires are also an option. Drawbacks of the standard guidewire design are that the length is not customized, limited unique patterns are available and materials of construction may result in too much artifact when in close proximity with other guidewires. It would be desirable to identify a method of lumen marking which overcomes the problems of the prior art.

SUMMARY

According to one aspect of the invention a system and method for enhancing the ability to visualize and identify lumens in a multi-lumen device involves modifying a feature of at least one lumen and/or modifying a feature of a member which couples the lumens.

In one embodiment, the features of the lumens which may be modified to distinguish the lumens includes, but is not limited to, a marking on the lumen, a diameter of the lumen and a composition of the lumen. For example, a multi-lumen brachytherapy device may comprise markings located on or about the multiple lumens to assist in the visualization and identification of the individual lumens during CT scans. In one embodiment at least one lumen in a multi-lumen brachytherapy device is printed with a unique pattern using radio-opaque ink. For example, the exterior surface of the printed lumen may be marked at its distal tip and then in a unique pattern down at least a portion of its length. With such an arrangement visualization of the tip of the lumen is achieved with reduced artifact. The 'built in' nature of the markings enables visualization without the addition of specialized accessories, reducing the overall transfer cost of the brachytherapy device. As will be described later herein, in alternative embodiments two or more of the lumens may be formed from material having a different radiographic contrast to distinguish the lumens during imaging or two or more lumens may have different diameters.

According to another aspect of the invention, a distal tip of the multi-lumen brachytherapy device comprises a connection member which couples the distal tips of the multiple lumens. In one embodiment certain features of the connection member may be altered to facilitate identification of the lumens, where the features that may be altered include but are not limited to the connection points between the lumens and the member, the body of the member and the composition of the member. For example, the distal tip may be formed to include one or more different markings at the different connection points of the individual lumens to allow differentiation of the lumens in a transverse (axial) CT scan image. Alternatively, a perimeter of the connection member may be marked at points related to lumen position to facilitate lumen identification. In still another embodiment the distal tips of the lumens may be distinguished by forming the connection member from a material having a different radiographic contrast than that of the lumens.

DETAILED DESCRIPTION

Systems and methods that facilitate visualization and identification of lumens of a multi-lumen brachytherapy device are disclosed. In one embodiment, visualization and identification can be attained by modifying a feature of at least one of the lumens relative to the other lumens. The feature may include a marking on the lumen, a diameter of the lumen or a composition of the lumen. In an additional embodiment, for brachytherapy devices in which multiple lumens are coupled to a distal end point such as a rigid connection member, visualization and identification of the lumens can be attained by modifying a feature of the rigid connection member. It will be readily appreciated that visualization and identification can be further enhanced through a combination of two or more of the techniques described herein.

Figure 1:
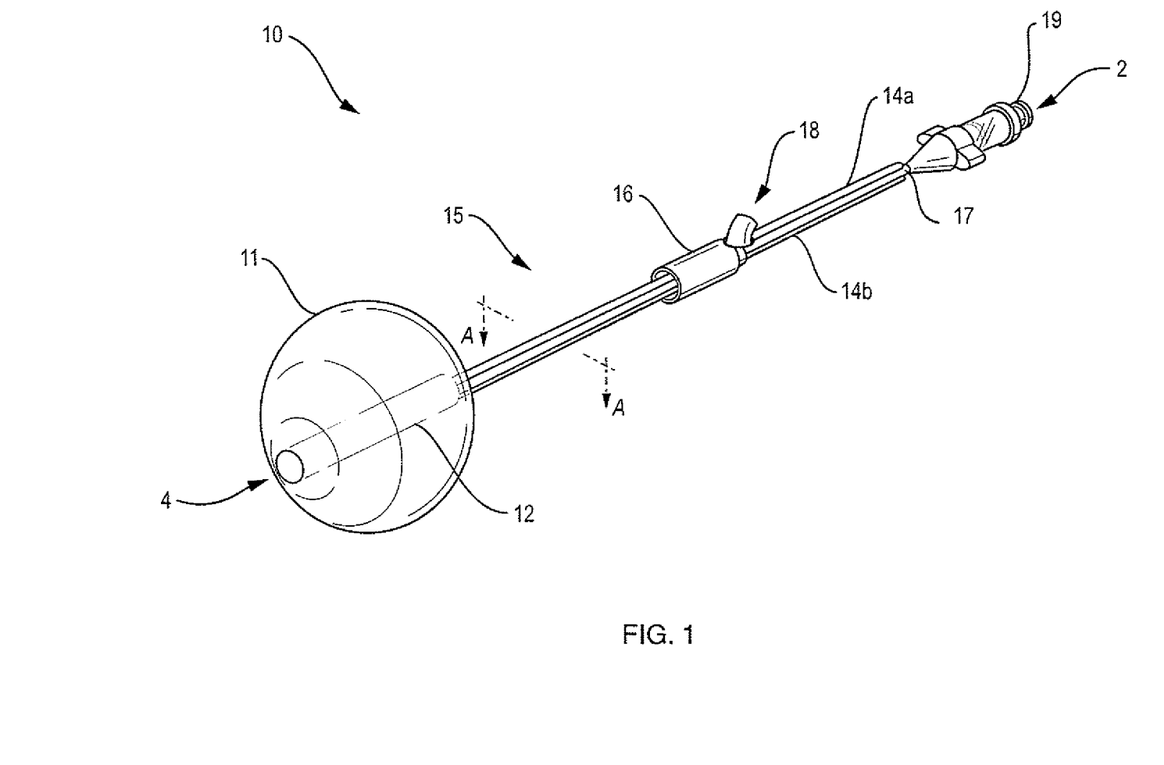
FIG. 1 illustrates a multi-lumen brachytherapy device which may be adapted using one or more of the principles of the present invention to facilitate visualization and identification of the lumens.

FIG. 1 illustrates an example of a multi-lumen brachytherapy catheter which may use one or more of the techniques of the present invention to distinguish lumens. A brachytherapy device 10 includes a flexible shaft 15 including a proximal end 2 and a distal end 4. The flexible shaft is comprised of a plurality of flexible dosing lumens 14a and 14b and an inflation lumen 17. Each dosing lumen is sized to accommodate one or more radiation sources for customization of radio-isotope treatment profiles. It should be noted that although only two dosing lumens are visible in FIG. 1, the present invention may be implemented with any number of dosing lumens. The inflation lumen 17 is coupled at a proximal end to a connector 19. The lumens 14a, 14b and 17 are made, for example, from flexible or semi-flexible types of extruded tubing. Each lumen 14a, 14b, 17 slideably extends through holes in the hub 16 and into openings which extend longitudinally into the rigid connection member 12. In one embodiment the openings in the rigid connection member are sized so that the exterior of each lumen is tightly received in its respective opening. The lumens may be fixedly attached to the rigid connection member 12 using an adhesive.

An inflatable member, shown as balloon 11, envelops at least a portion of the rigid connection member 12. In operation, the inflatable member is inflated by coupling the device to a source of a gas or other liquid via connector 19. The inflation liquid flows into the member via the inflation lumen 17. One or more inflation holes (not shown) extend through the inflation lumen and rigid connection member into the inflatable member. When the inflatable member is positioned in the resected cavity, the gas or other liquid is forwarded through the inflation lumen into the inflatable member to secure the member within the cavity. Once the member is inflated, connector 19 is detached from the source.

The hub 16 collects but does not connect the lumens; in some embodiments, the portion of the flexible shaft between a distal end of the hub and a proximal end of the rigid balloon section may be sheathed in a catheter, although it is not a requirement of the invention. The hub 16 includes one or more holes extending there through, where the holes in the hub have clearance tolerances that allow the lumens to independently move axially and rotatably within the hub.

Because the multiple lumens of the device 10 are flexible and independently moveable both axially and rotationally, forces experienced at the proximal end of the device 10 do not translate into movement at the distal end of the device. Reducing the propensity for movement of the shaft also increases the comfort of the patient.

Clear visualization and identification of the lumens is important to dosimetry planning and implementation but is difficult due to the close spacing of the lumens. As described above the present invention facilitates the visualization and identification through modification of one or more features of the lumens or connection member as will be described with reference to FIGS. 2-7.

Figure 2:
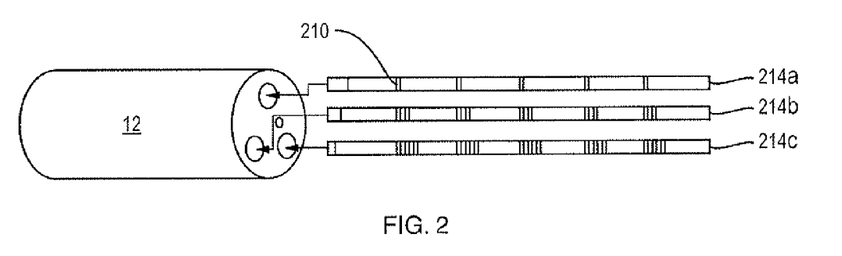
FIG. 2 illustrates a plurality of lumens of the present invention which are printed in various patterns to increase visualization and identification.
Figure 3:
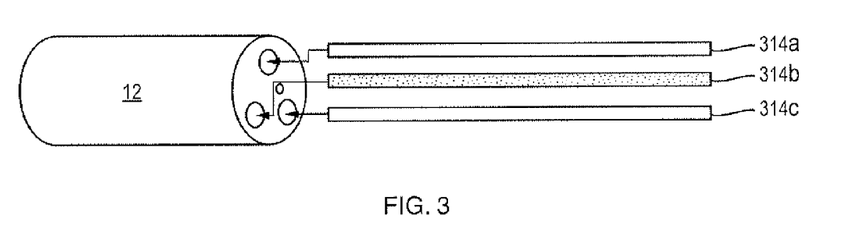
FIG. 3 illustrates a plurality of lumens of the present invention which are formed from material having different radiographic contrast.
Figure 4:
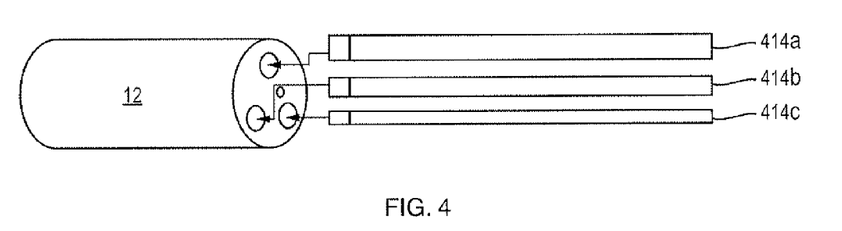
FIG. 4 illustrates another embodiment whereby the feature of each lumen that differs is their diameter.

FIGS. 2-4 illustrate how features of the lumens may be modified to visually differentiate them for identification purposes. As shown in FIG. 2, each of the dosing lumens 14a, 14b and 14c are uniquely marked with radio-opaque ink, for example each having a different pattern of radio-opaque markings 210. For example Radio-opaque™ Ink developed by CI Medical Inc., of Norton Mass. or other equivalent may be used. In one embodiment, the exterior surface of each lumen is printed at the tip and along its length with its individual pattern prior to coupling to the rigid member. As a result visualization of the tip and differentiation of the lumens may be achieved without additional guide wires or accessories. In one embodiment the markings may be made at pre-defined increments (cm, mm) to provide reference measurement points to users for placement and observation of radioactive material. One advantage of using radio-opaque ink, as opposed to wrapping the lumen with wire or other radio-opaque material is that the device is lighter and there is no chance that the markers may change positions.

In an alternative embodiment illustrated in FIG. 3 the lumens 314a, 314b, 314c may be made of material having different radiographic contrast (measured in terms of Hounsfield units) to maximize contrast and clarity between the lumens and reduce material artifact.

FIG. 4 illustrates another embodiment whereby the feature of each lumen that differs is their diameter. The use of a lumen with a different diameter and comprised of a material sufficient to be provide imagable contrast, may be used in conjunction with a marker at the tip of the lumen to visualize the lumen tip as well as differentiate the lumens, as the relative diameters will be readily ascertainable in the resulting image.

Figure 5A:
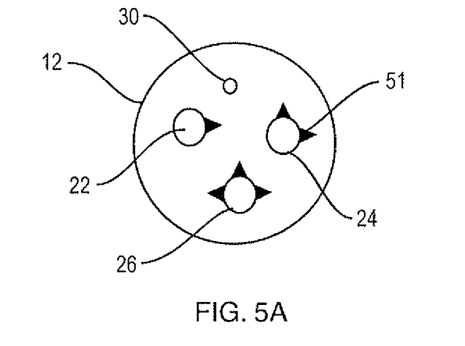
FIGS. 5A-5C illustrate a variety of embodiments for marking a rigid portion of the brachytherapy device of FIG. 1 to assist in the visualization and identification of the lumens.
Figure 5B:
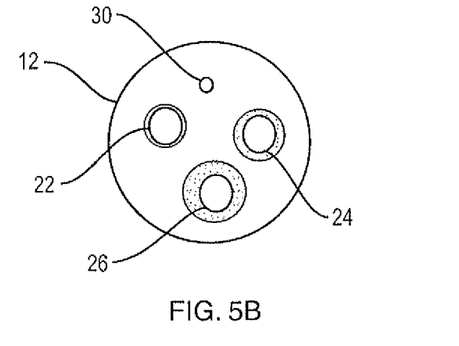
Figure 5C:
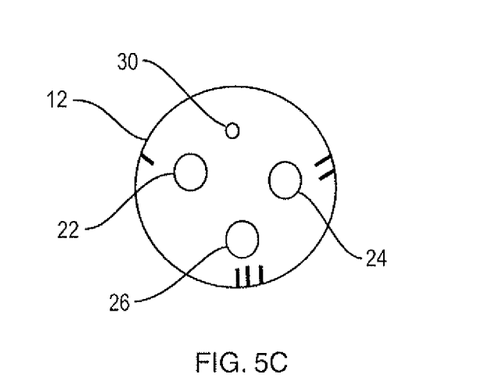

FIGS. 5A-5C are cross-section images of the rigid member, take along plane A of FIG. 1. It is known that different elements have different radiographic contrast (measured in Hounsfield units) which provides a resultant image that is either lighter or darker. As a reference, water is 0H, Air is −1000H (appears darker) and Titanium is +1000H (appears lighter). According to one aspect of the invention it is realized that the rigid member may be formed with features that capture air. The features may surround the openings into which the lumens are extended so that cross-sectional views, identifiable via a transverse CT scan, will display the features and facilitate identification of the individual lumens. Alternatively the features may be cut into the rigid connection member, either on the periphery, or as through holes, etc., in positions that are proximate to the lumens.

FIGS. 5A and 5B illustrate embodiments wherein the features are positioned near the openings of the member which connect to the lumens. In one embodiment the connection member is formed a photosensitive resin using stereolithography to define the dosing lumen openings 22, 24 and 26 and inflation lumen opening 30. Alternatively the connection member could be machined, or the part may be formed using an extrusion process. The openings in FIG. 5A are sized in accordance with the diameter of the lumens to form a tight fit between the lumens and the connection device. In addition notches 51 may be drilled at the edges of the openings. Each opening may have a different number of notches ranging from 0 to N, where N is the number of openings. The air pocket that is naturally within each notch provides a dark marking on the scan image, allowing individual lumens to be identified with ease.

FIG. 5B illustrates a different embodiment where the lumen opening size is varied for lumen identification. For example, lumen opening 22 is smallest, lumen opening 24 is medium and lumen opening 26 is largest. In such an embodiment, the lumen is coupled to the rigid member using an adhesive at its tip, and an air pocket is therefore formed around the lumen within the rigid member. As shown in FIG. 5B the air pockets that result from the different size openings allow the individual lumens to be distinguished.

FIG. 5C illustrates an embodiment wherein the peripheral body of the connection member is scored with notches. The location of scoring relates to the location of the lumen holes; it need not directly relate as long as the relation is known to the observer. As shown in FIG. 5C scoring is different for each lumen location.

Other methods of notching, scoring or modifying the connection member to generate air pockets that can be visualized to distinguish the lumens include drilling holes of varying sizes proximate to each lumen hole, scoring different shapes at the peripheries (box, arc, x, etc.) and the like.

Figure 6:
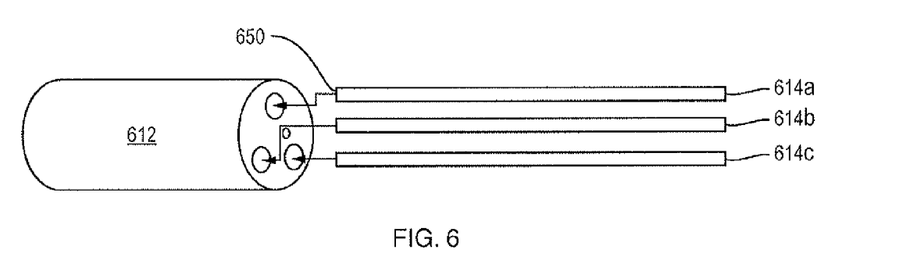
FIGS. 6 and 7 illustrate the rigid portion of the catheter and the lumens having differing radiographic contrast.
Figure 7:
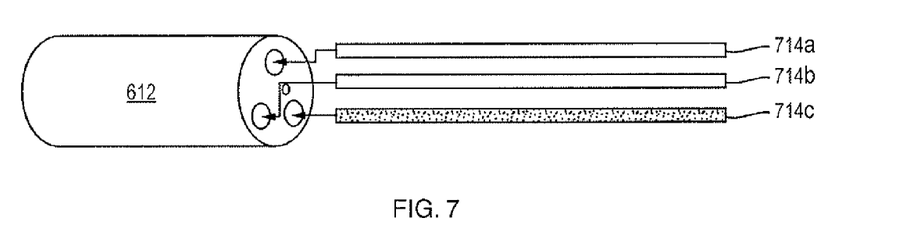

FIGS. 6 and 7 illustrate embodiments of the invention where the composition of the lumen and connection member is selected to facilitate location of the distal tip 550 of the lumen. In FIGS. 6 and 7 the shading of the element is related to the radiographic contrast of the element; in FIG. 6 the lumens are of a higher contrast than the connecting member and the intersection of the two different types of materials allows the endpoint of the lumen to be identified with increased precision. In FIG. 7, in addition to the connection member, each of the lumens is made from a material having a different contrast, helping to distinguish the lumens from each other as well as enhancing end point identification.

Accordingly, a method of making a multi-lumen catheter device may include adding features to either of the lumens or a member connecting the lumens to enhance lumen visualization and identification. The methods include printing the lumens distinct patterns using radio-opaque ink and/or manufacturing the lumens using materials of differing radiographic contrast. The methods also include adding a feature to the connection member during its formation, where the feature includes one of notches, holes or other removal of material of the connection member near or about lumen connection points to form air gaps in the connection member, such air gaps being used for identification of the lumens and visualization of lumen end point locations.

Having described several preferred embodiments of the invention it should be appreciated that there are many ways in which the concepts of the present invention may be combined to provide a multi-catheter device with improved visibility. All of the combinations are within the scope of the present invention. In addition although certain materials are disclosed it should be noted that the materials are provided merely by way of example and the present invention may be practiced with a variety of equivalent substitute materials. In addition, although the invention has been described with regard to a breast brachytherapy device it is appreciated that the concepts may be extended for use in any device that requires precise imaging information.

Although various exemplary embodiments of the invention have been disclosed, it should be apparent to those skilled in the art that various changes and modifications can be made that will achieve some of the advantages of the invention without departing from the true scope of the invention. These and other obvious modifications are intended to be covered by the appended claims.

The invention claimed is:

1. A multi-lumen treatment device comprising:
a rigid member fixed at a distal end of the treatment device, the rigid member having a proximal end and a distal end and defining therein a plurality of openings parallel to each other and extending longitudinally from the proximal end of the rigid member towards the distal end of the rigid member in which each of the plurality of openings is open only at the proximal end of the rigid member;
an inflatable member enveloping at least a portion of the rigid member; and
a plurality of separate dosing lumens, each having a proximal end and a distal end, wherein each distal end of each dosing lumen extends into a different one of the plurality of openings of the rigid member to retain the respective dosing lumen throughout the respective opening such that each dosing lumen is coupled to the rigid member such that the rigid member is fixed in position relative to each dosing lumen, and wherein the rigid member includes at least one feature for identifying at least one characteristic of at least one dosing lumen is disposed on the rigid member.

2. The multi-lumen treatment device of claim 1 wherein the at least one feature is a radiographic contrast of a material of the rigid member that differs from a radiographic contrast of the at least one dosing lumen and the identified characteristic of the at least one dosing lumen is the endpoint of the dosing lumen.

3. The multi-lumen treatment device of claim 1 wherein the at least one feature is a notch located proximate to the opening that is related to the at least one dosing lumen and the identified characteristic of the at least one dosing lumen is an identity of the dosing lumen.

4. The multi-lumen treatment device of claim 3 wherein the notch is at an edge of the opening.

5. The multi-lumen treatment device of claim 4 wherein each of the openings has a different pattern of notches.

6. The multi-lumen treatment device of claim 3 wherein the notch is positioned on an exterior surface of the rigid member proximate to the at least one dosing lumen.

7. The multi-lumen treatment device of claim 6 wherein a plurality of different notch patterns are positioned on the exterior surface of the rigid member, each pattern proximate to a different opening.

8. The multi-lumen treatment device of claim 1 wherein the at least one feature includes a size of the plurality of openings, wherein the openings are differently sized and the size is associated with an identify of the dosing lumen.

9. A multi-lumen balloon catheter for treating breast cancer comprising:
a plurality of dosing lumens for delivering radioactive treatment to a breast, each dosing lumen having a proximal end and distal end;
an inflation lumen;
a connection member coupling the plurality of dosing lumens and fixed at a distal end of the catheter, the connection member having a proximal end and a distal end and defining therein a plurality of openings parallel to each other and extending longitudinally from a proximal end of the connection member towards a distal end of the connection member in which each of the plurality of openings is open only at the proximal end of the connection member, wherein each distal end of each dosing lumen extends into a different one of the plurality of openings of the connection member to retain the respective dosing lumen through the respective opening such that each dosing lumen is coupled to the connection member such that the connection member is fixed in position relative to each dosing lumen, and wherein at least one feature for identifying at least one characteristic of at least one dosing lumen is disposed on the connection member; and
an inflatable member disposed over the distal ends of the plurality of dosing lumens and enveloping at least a portion of the connection member, wherein the inflatable member is coupled in flow communication to the inflation lumen for inflating the inflatable member.

10. The multi-lumen balloon catheter of claim 9 wherein the feature of the connection member identifies the dosing lumen.

11. The multi-lumen balloon catheter of claim 9 wherein the feature of the connection member identifies the inflation lumen.

12. The multi-lumen balloon catheter of claim 9 wherein the feature of the connection member is a radiographic contrast of a material of the connection member which differs from a radiographic contrast of a material of at least one of the lumens to facilitate visualization of the distal ends of the lumens.

13. The multi-lumen balloon catheter of claim 9 wherein the at least one feature of the connection member provides an air gap that may be visualized using a computed tomography (CT) scan.

14. The multi-lumen balloon catheter of claim 13 wherein the air gap is provided via a notch in the connection member.

15. The multi-lumen balloon catheter of claim 14 wherein the notch is located proximate to one of the dosing lumens and is provided to identify the one dosing lumen.

16. The multi-lumen balloon catheter of claim 15 wherein the notch is located at a connection point of the one dosing lumen.

17. The multi-lumen balloon catheter of claim 15 wherein the notch is located on an exterior surface of connection member proximate to the one dosing lumen.

18. The multi-lumen balloon catheter of claim 13 wherein the air gap is provided around the lumen when the lumen is connected to the connection member.

* * * * *